US008403671B2

(12) United States Patent
Lin (10) Patent No.: US 8,403,671 B2
(45) Date of Patent: Mar. 26, 2013

(54) DETACHMENT-PREVENTED REMOVABLE DOUBLE-CROWN PROSTHETIC APPLIANCE

(76) Inventor: Tai-Wu Lin, Taipei (TW)

( * ) Notice: Subject to any disclaimer, the term of this patent is extended or adjusted under 35 U.S.C. 154(b) by 406 days.

(21) Appl. No.: 12/828,300

(22) Filed: Jul. 1, 2010

(65) Prior Publication Data

US 2012/0003607 A1    Jan. 5, 2012

(51) Int. Cl.
*A61C 5/08* (2006.01)
(52) U.S. Cl. ......................... 433/218; 433/193
(58) Field of Classification Search .......... 433/167–172, 433/177–178, 181–183, 191–195, 206–212.1, 433/218–221
See application file for complete search history.

(56) References Cited

U.S. PATENT DOCUMENTS

| | | | | |
|---|---|---|---|---|
| 1,884,128 A * | 10/1932 | Myerson | ...................... | 433/177 |
| 2,574,330 A * | 11/1951 | Judd | .............................. | 403/107 |
| 2,669,779 A * | 2/1954 | Zuccoli | ........................ | 433/193 |
| 2,744,326 A * | 5/1956 | Chaiken et al. | ............... | 433/223 |
| 2,799,933 A * | 7/1957 | Neustadter | .................... | 433/183 |
| 2,868,489 A * | 1/1959 | Calcut | ...................... | 248/229.26 |
| 3,514,858 A * | 6/1970 | Silverman | ..................... | 433/174 |
| 3,719,378 A * | 3/1973 | Windsor | ........................ | 403/289 |
| 4,380,436 A * | 4/1983 | Kipp | .............................. | 433/182 |
| 4,773,859 A * | 9/1988 | Obersat | ........................ | 433/177 |
| 5,194,002 A * | 3/1993 | Obersat | ........................ | 433/182 |
| 5,275,560 A * | 1/1994 | Obersat | ........................ | 433/177 |
| 5,435,043 A * | 7/1995 | Ito et al. | ........................ | 24/114.4 |
| 6,170,129 B1 * | 1/2001 | Pferdehirt | ....................... | 24/108 |
| 6,171,107 B1 * | 1/2001 | Milne | ............................. | 433/189 |
| 7,059,854 B2 * | 6/2006 | Wu | ................................ | 433/173 |
| 7,490,727 B2 * | 2/2009 | Spiers et al. | ............... | 211/89.01 |
| 8,099,837 B2 * | 1/2012 | Santin et al. | ..................... | 24/297 |
| 2004/0151539 A1 * | 8/2004 | Sikora et al. | .................. | 403/329 |
| 2005/0053894 A1 * | 3/2005 | Wu | ................................ | 433/18 |
| 2005/0074725 A1 * | 4/2005 | Wu | .............................. | 433/223 |
| 2007/0105067 A1 * | 5/2007 | Hayashi et al. | ............... | 433/172 |

* cited by examiner

*Primary Examiner* — Cris L Rodriguez
*Assistant Examiner* — Hao D Mai
(74) *Attorney, Agent, or Firm* — Leong C. Lei (57) ABSTRACT

A detachment-prevented removable double-crown prosthetic appliance includes an internal crown member, which has an outside surface to which two resilient retention clamping strips are mounted, each of the resilient retention clamping strips including a root section that is fixed to the outside surface of the internal crown member and a spring section extending from the root section, the spring sections of the resilient retention clamping strips being spaced by a gap that has a reduced neck portion forming a pass; and an external crown member, which is removably mounted to the internal crown member and has a lower inner portion forming a fitting chamber for removably fitting over the internal crown member, the fitting chamber having an inside surface that forms a retention block that is engageable with the resilient retention clamping strips so as to securely but removably couple the external crown member to the internal crown member.

14 Claims, 9 Drawing Sheets

DETACHMENT-PREVENTED REMOVABLE DOUBLE-CROWN PROSTHETIC APPLIANCE

TECHNICAL FIELD OF THE INVENTION

The present invention generally relates to a prosthetic crown, and more particularly to a detachment-prevented removable double-crown prosthetic appliance, which comprises an internal crown member that is bonded to a tooth abutment of a patient and an outer crown member that is removably fit to the internal crown member in such a manner that the internal and external crown members are securely retained together to eliminate the potential risk that the external crown member is easily detachable from the internal crown member, so that the prosthetic appliance can be removed for throughout cleaning of the internal and external crown members and the adjacent teeth are provided with a safety latch to securely hold the external crown member in position to prevent the external crown member to be removed as being stuck by sticky food stuffs, thereby ensuring safety, convenience and ease of a user using the prosthetic appliance.

DESCRIPTION OF THE PRIOR ART

A human body contains various organs, which are of diverse lives. Taking the digestive system as an example, a person rarely faces any potential risk of decay of anus even the person lives to 60 or 70 years old. However, the teeth of human beings are often damaged due to dental caries or tooth decay when aged 30 or 40 so that some of the teeth must be extracted and substituted by prosthetic teeth. It is generally due to that the form and structure of teeth in the oral cavity make it difficult to efficiently and effectively cleanse the teeth. The teeth are located inside the oral cavity and cannot be removed for cleansing, so that there are corners or locations where cleaning cannot be effectively performed. For example, it is difficult, if not possible, to clean gingival sulcus and crevices between teeth.

In the past century dentistry has progressed to quite an extent. However, prosthetic teeth are still mounted to a patient's mouth through bonding or cementing and the existing prostheses are of more drawbacks than the natural teeth, making it not possible to protect teeth from decaying and extraction. Recently, dental implanting is prevalent and this fact indicates that the conventional dental treatment and the existing fixed dentures are not effective therapeutics.

For the existing restoration of teeth using prostheses, the decayed tooth is extracted or adjacent virgin teeth are processed to serve as abutment to support and fix the arrangement of prostheses. It is reasonably desired for a novel prosthetic appliance that is removable from the oral cavity for efficient performance of complete cleaning (of both the prostheses and the natural teeth), rather than the fixed type dentures that are similar to the natural teeth in that they both are not removable from the oral cavity for efficient and effective cleaning.

This is the reason that a German dentistry professor invented double crown prostheses 30 years ago, in which internal and external crowns are fixed together through surface frictional force, so that removal can be made for cleaning purposes. Due to the difficulty found in the manufacture and use of the German prosthetic appliance, especially for the problem discussed below, the double crown are now not manufactured in Japan and are only used by very few dentists in Germany. The double crown suffers retention stability for the external crown when the patient eats sticky food stuffs. The German double crown depends on frictional forces for retention, but such an arrangement is problematic in that it is either too tight, making it hard to remove the prosthesis, or too loose, making it easily removed by being stuck to sticking food stuffs.

Thus, it is desired to provide a novel structural arrangement of double-crown prosthetic appliance in order to eliminate the problems discussed above.

Dental caries is one of the most commonly seen problems in dentistry. In case of extensive tooth decaying, severe cavities are found in the surfaces of teeth, making it impossible to completely restore the function of mastication. It is thus a solution to use a dental crown fit to the exterior of a decayed tooth for normal appearance and mastication. To install the crown, with the decayed tooth extracted, adjacent natural teeth must be also processed to reduce the size for mounting for example a bridge that is often of a three-unit (or multiple-unit) structure.

The existing crowns or bridges are bonded to abutment teeth by a dental bonding agent (such as cement) and the crown and the abutment teeth so bonded together are not allowed to separate again. However, for such a fixed crown that is mounted in such a non-separated manner, once the crown is damaged due to abrasion or corrosion caused by or in combination with damage of tooth root or periodontal sulcus, it is not possible to remove and replace the crown.

A removable crown assembly is also available, and it comprises an internal crown bonded to a tooth abutment and a removable external crown fit to the internal crown. This allows the external crown to be removed for cleaning the abutment tooth and the external crown. The external crown can be removed for repairing when it is damaged. This improves the efficiency of repairing of the crown assembly. However, the external crown is designed to be held in position through frictional forces and this makes it not possible to securely and tightly retain the external crown on the internal crown, leading to such a problem that the external crown may be undesired removed due to the user masticates sticky food stuffs or the external crown is retained over-tightly and is extremely hard to be removed. Due to such problems, the external crown requires additional fastening means.

SUMMARY OF THE INVENTION

In view of the above problems that the abutment teeth and the periodontal bones of a fixedly bonded crown cannot be properly cleaned, leading to corrosion, the present invention aims to provide a detachment-prevented removable double-crown prosthetic appliance to overcome the above problems and drawbacks.

The primary objective of the present invention is to provide a detachment-prevented removable double-crown prosthetic appliance, which comprises an internal crown member and an external crown member. The internal crown member is bonded to a tooth root of a patient, while the external crown member is removably fit over the internal crown member in such a way that the internal and external crown members are sufficiently stably but not over-tightly coupled to each other so that the external crown member is prevented from detachment from the internal crown member. In this way, the prosthetic appliance can be removed for throughout cleaning of the internal and external crown members and the adjacent natural teeth as desired and since the external crown member is securely held in position by a safety latch, the external crown member is not allowed to easily detach when a patient wearing the prosthetic appliance is chewing a sticky food stuff, thereby ensuring safety, convenience, and ease of the patient wearing the prosthetic appliance.

To achieve the above objective, the present invention provides a detachment-prevented removable double-crown prosthetic appliance, comprising:

an internal crown member, which has an outside surface to which two resilient retention clamping strips are mounted, each of the resilient retention clamping strips comprising a root section that is fixed to the outside surface of the internal crown member and a spring section extending from the root section, the spring sections of the resilient retention clamping strips being spaced by a gap that has a reduced neck portion forming a pass; and an external crown member, which is removably mounted to the internal crown member and has a lower inner portion forming a fitting chamber for removably fitting over the internal crown member, the fitting chamber having an inside surface that forms a retention block that is engageable with the resilient retention clamping strips by moving through the pass so as to force the spring sections of the resilient retention clamping strips to expand and deform outward, the spring sections allowing to return after the retention block moves through the pass to shrink back to clamp and thus retain the retention block, whereby the external crown member is securely coupled to the internal crown member in such a way that the external crown member is not allowed to undesirably detach.

With the above technical solution, due to the engagement established between the resilient retention clamping strips and the retention block that securely holds the internal and external crown members together, the coupling between the internal and external crown members is enhanced. The problem that the external crown member is undesirably detached due to a patient chewing sticky food stuffs can be eliminated, but the user is allowed to remove the external crown member from the internal crown member by applying a vertical force thereto for throughout cleaning of the external crown member, as well as cleaning of the abutment tooth, periodontal area, and adjacent teeth. In this way, undesired detachment of the crown can be eliminated.

In the detachment-prevented removable double-crown prosthetic appliance of the present invention, each of the resilient retention clamping strips comprises a spring force enhancing section extending from the root section and located outside the spring section, and the inside surface of the external crown member forms two inward projecting inclined support surfaces, which are respectively engageable with the two spring force enhancing sections of the resilient retention clamping strips for providing additional spring forces.

In the detachment-prevented removable double-crown prosthetic appliance of the present invention, each of the spring sections is of an L-shape having a bend, and the bends of the two spring sections oppose each other to define the pass.

In the detachment-prevented removable double-crown prosthetic appliance of the present invention, the resilient retention clamping strips are made of a metallic material or a resilient material.

In the detachment-prevented removable double-crown prosthetic appliance of the present invention, the resilient retention clamping strips are made of a metallic material that is selected from a group consisting of carat gold, dentistry alloys, stainless steels, nickel-titanium alloys and a combination thereof.

In the detachment-prevented removable double-crown prosthetic appliance of the present invention, the external crown member and the internal crown member are made of metallic materials or resilient materials.

In the detachment-prevented removable double-crown prosthetic appliance of the present invention, the root section of each of the resilient retention clamping strips has a fixed end, which is integrally formed with the outside surface of the internal crown member.

In the detachment-prevented removable double-crown prosthetic appliance of the present invention, the root section of each of the resilient retention clamping strips has a fixed end, which is mounted to the outside surface of the internal crown member through welding, pressing, or bonding.

In the detachment-prevented removable double-crown prosthetic appliance of the present invention, the internal crown member comprises a fixing element that fixes the root sections of the resilient retention clamping strips in position.

In the detachment-prevented removable double-crown prosthetic appliance of the present invention, the fixing element is made of metallic materials, fiber-reinforced plastics, or resins.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Referring to FIGS. 1-4, a detachment-prevented removable double-crown prosthetic appliance constructed in accordance with a first embodiment of the present invention is mountable to a decayed tooth 91 of the gingiva 90 of a patient.

The removable double-crown prosthetic appliance of the present invention comprises an internal crown member 10 and an external crown member 20.

The internal crown member 10 is preferably made of a metallic material and has an outside surface 100 to which two resilient retention clamping strips 15 are mounted. Each of the resilient retention clamping strips 15 comprises a root section 151 that is fixed to the outside surface 100 of the internal crown member 10 and a spring section 152 extending from the root section 151. The spring sections 152 of the two resilient retention clamping strips 15 are spaced from each other by a gap, of which a narrowest portion forms a pass 16. Further, the spring section 152 is of an L-shape, having a bend 1520, whereby the bends 1520 of the two spring sections 152 oppose each other and define the pass 16. Further, the resilient retention clamping strips 15 are made of a metallic material, or alternatively, they can be made of carbon fibers, fiber-reinforced plastics, resins, or other suitable materials. The material making the resilient retention clamping strips 15 are preferably selected from a group consisting of carat gold (such as 16-carat gold), stainless steel, alloys, nickel-titanium alloys or any combinations thereof, or any alloy that is approved by government agency. The root section 151 of each of the resilient retention clamping strips 15 has a lower end that is a fixed end 150, preferably integrally formed with and thus fixed to the outside surface 100 of the internal crown member 10, or alternatively, the fixed end 150 is mounted to the outside surface 100 of the internal crown member 10 through welding, pressing, or bonding. The nickel-titanium alloy mentioned previously is a so-called memory alloy, which can return to its original shape even subjected to a significant bending and such a characteristic help the practice of the present invention.

The external crown member 20 can be made of metallic materials, carbon fibers, fiber-reinforced plastics, or resins, and is structured to removably fit over and thus couple to the internal crown member 10. The external crown member 20 has a lower inner portion forming a fitting chamber 21 that allows the external crown member 20 to be removably fit over and thus coupled to the internal crown member 10. The fitting chamber 21 has an inside surface 210, which forms a retention block 23 that is engageable with and is thus retained by the resilient retention clamping strips 15. Preferably, the retention block 23 is of a circular cross-section, which, when moving downward to pass through the pass 16 between the two resilient retention clamping strips 15, help forcing the spring section 152 to expand and deform outward and the expanding the pass 16 for easy passing of the retention block 23. Once the retention block 23 moves through the pass 16, the spring sections 152 return to their original positions and shrink the pass 16 back to the original size to thereby clamp and retain the retention block 23, so that the external crown member 20 is fixed to the internal crown member 10.

Figure 4:
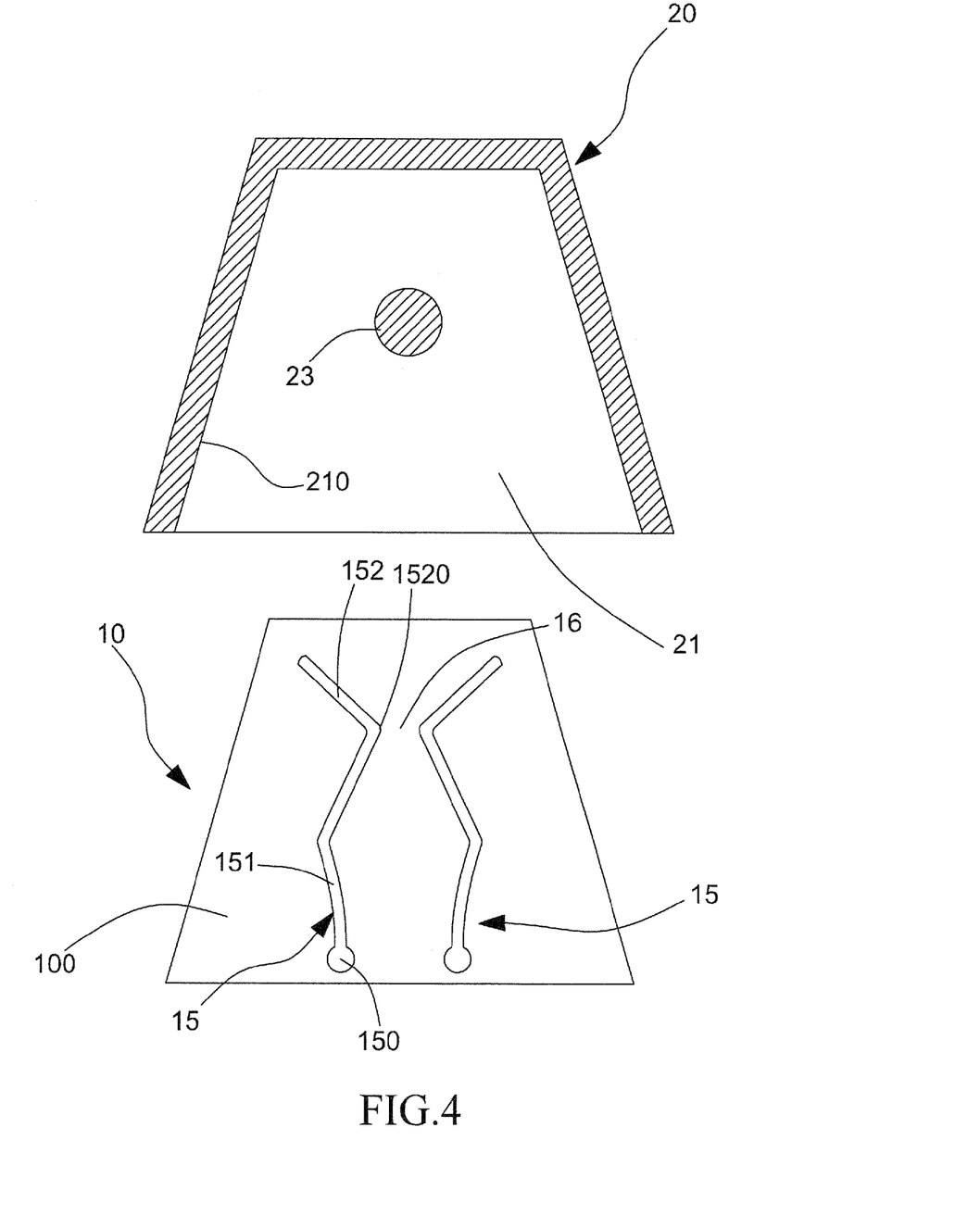
FIG. 4 is an exploded view, in a cross-sectional form, of the first embodiment of the present invention.
Figure 4A:
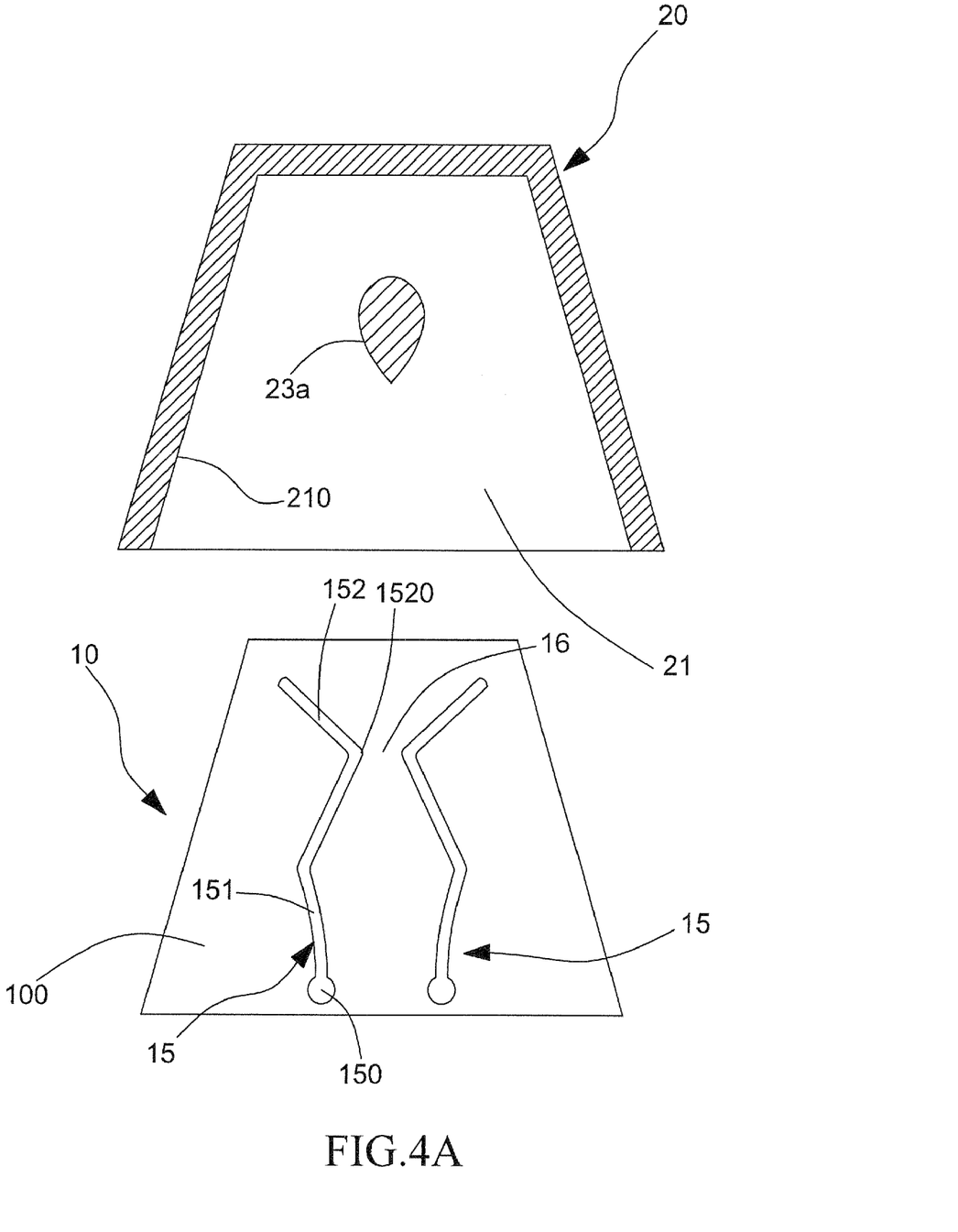
FIG. 4A is a cross-sectional view showing a modification of the first embodiment of the present invention.

Referring to FIG. 4A, in a modified embodiment, the external crown member 20 forms a water droplet like retention block 23a, of which a cross-sectional shape has a rounded top portion and a converging lower portion. Such a shape allows easy passing of the retention block 23a through the pass 16 to be clamped by the resilient retention clamping strips 15, and prevents the retention block 23a from moving upward to separate from the resilient retention clamping strips 15.

Figure 5:
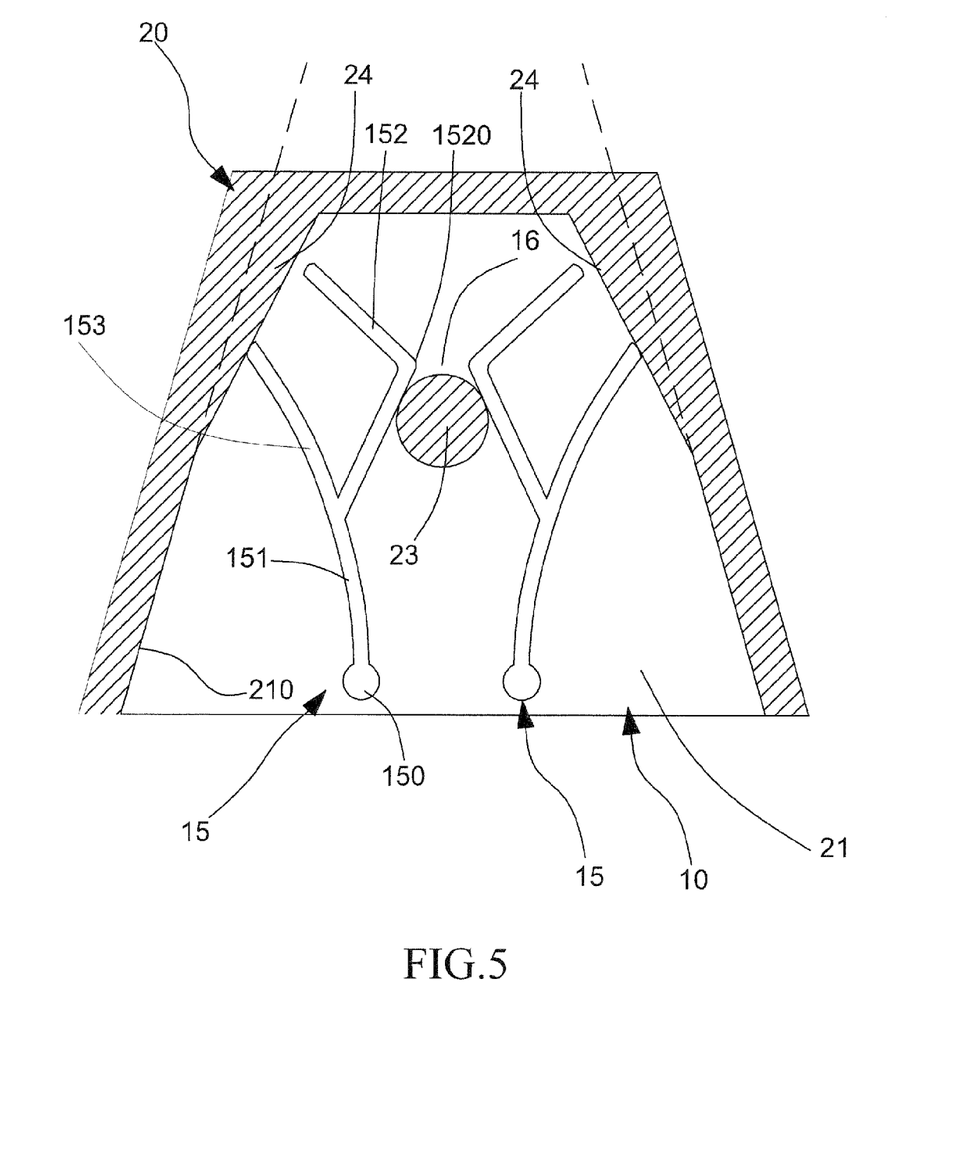
FIG. 5 is a cross-sectional view showing a second embodiment of the present invention.
Figure 6:
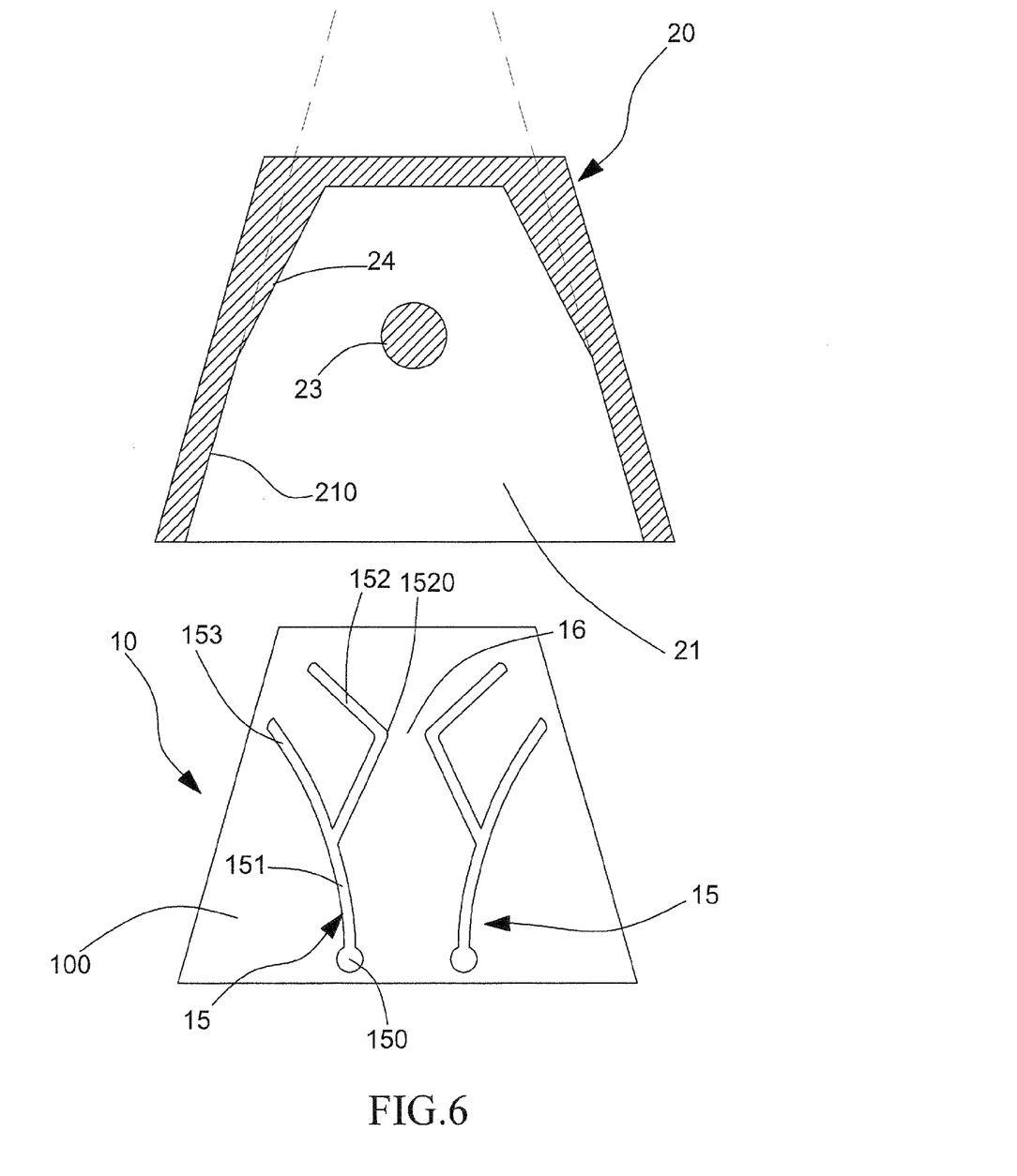
FIG. 6 is an exploded view, in a cross-sectional form, of the second embodiment of the present invention.

Referring to FIGS. 5 and 6, a detachment-prevented removable double-crown prosthetic appliance constructed in accordance with a second embodiment of the present invention is shown, wherein each of two resilient retention clamping strips 15 has a root section 151 from which a spring force enhancing section 153 extends upward to be located besides a spring section 152 that also extends from the root section 151. The external crown member 20 has an inside surface 210 having portions projecting inward to form two inclined support surfaces 24. The two inclined support surfaces 24 are respectively in contact with the two spring force enhancing sections 153 of the resilient retention clamping strips 15 to provide spring forces additional to the spring sections 152 for eliminating potential risks of elastic fatigues of the spring sections 152. The spring force enhancing sections 153 are provided in a condition where the resilient retention clamping strips 15 are not made of the nickel-titanium alloy. However, even though the resilient retention clamping strips 15 are made of the nickel-titanium alloy, the spring force enhancing sections 153 may be additionally provided. Further, the spring sections 152 and the spring force enhancing sections 153 can be properly compressed or deformed to change orientations thereof for regulating the tensile forces of the resilient retention clamping strips 15.

Further, the resilient retention clamping strips 15 are structured to allow for fine adjustment. When it is found that the resilient retention clamping strips 15 are over-relaxed, making it impossible to securely retain the internal crown member 10 and the external crown member 20 together, a tool can be used to expand a V-shaped included angle between the spring section 152 and the respective spring force enhancing section 153 to make the spring force enhancing section 153 inducing an enlarged spring force that enlarges a clamping force that the spring section 152 may have for the retention block 23. In this way, the tightness of retention between the external crown member 20 and the internal crown member 10 can be adjusted.

Figure 1:
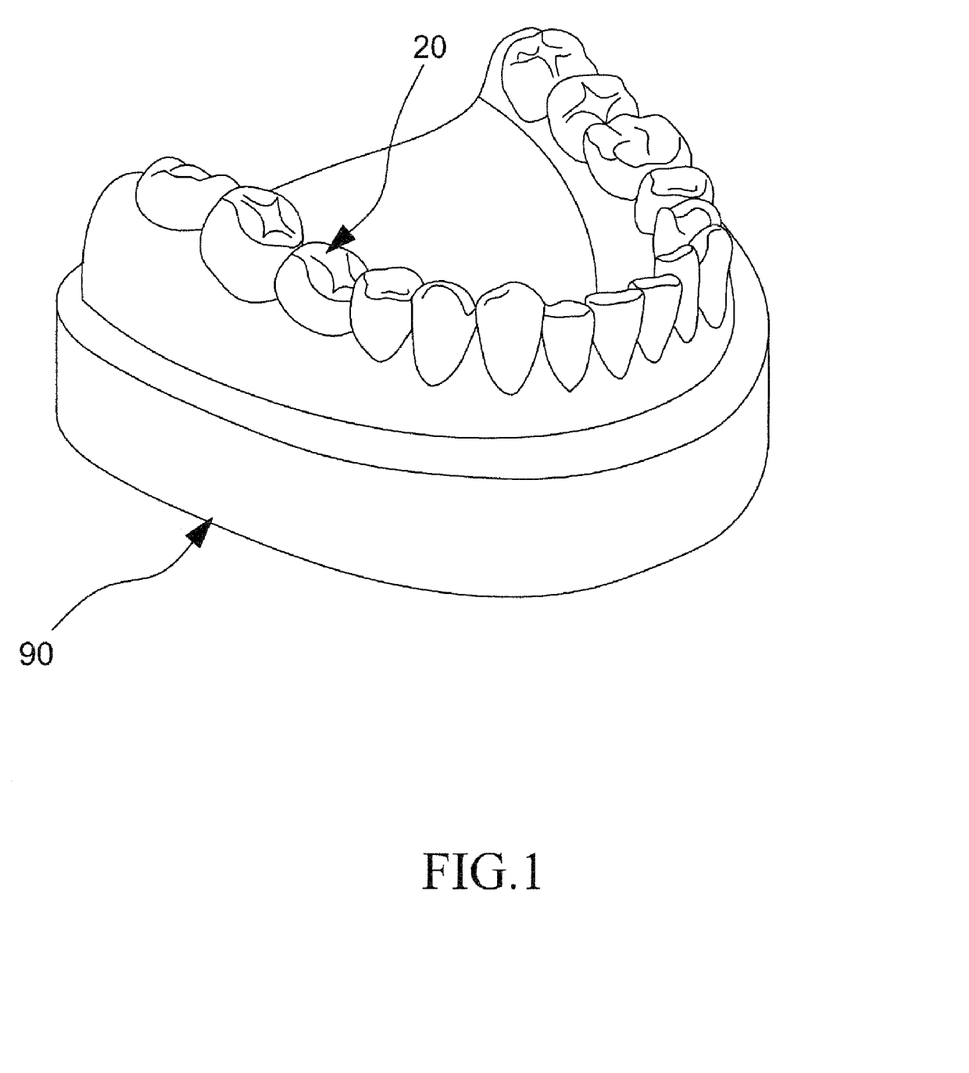
FIG. 1 is a perspective view showing a first embodiment of the present invention and gingiva of a patient.
Figure 2:
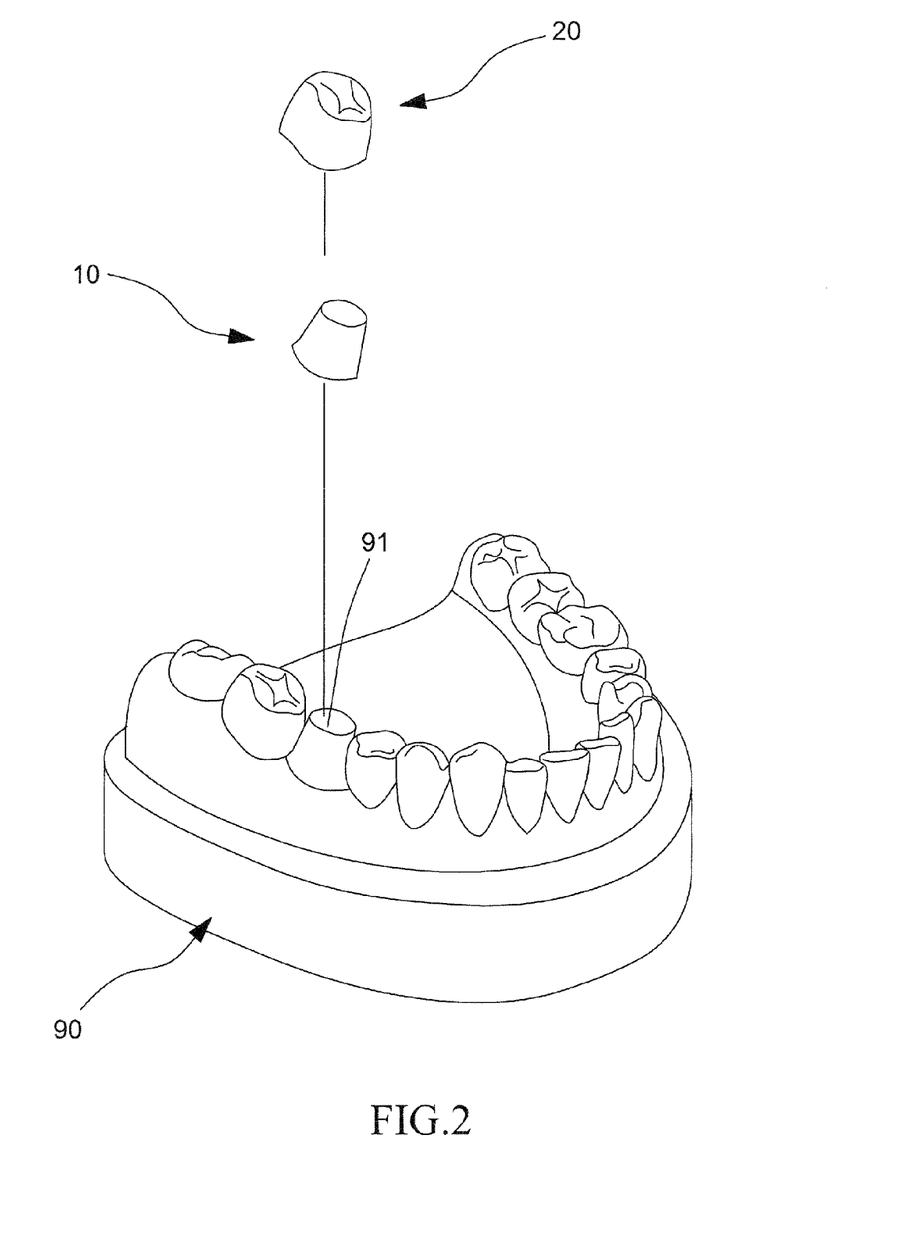
FIG. 2 is an exploded view showing the first embodiment of the present invention and the gingiva of the patient.
Figure 3:
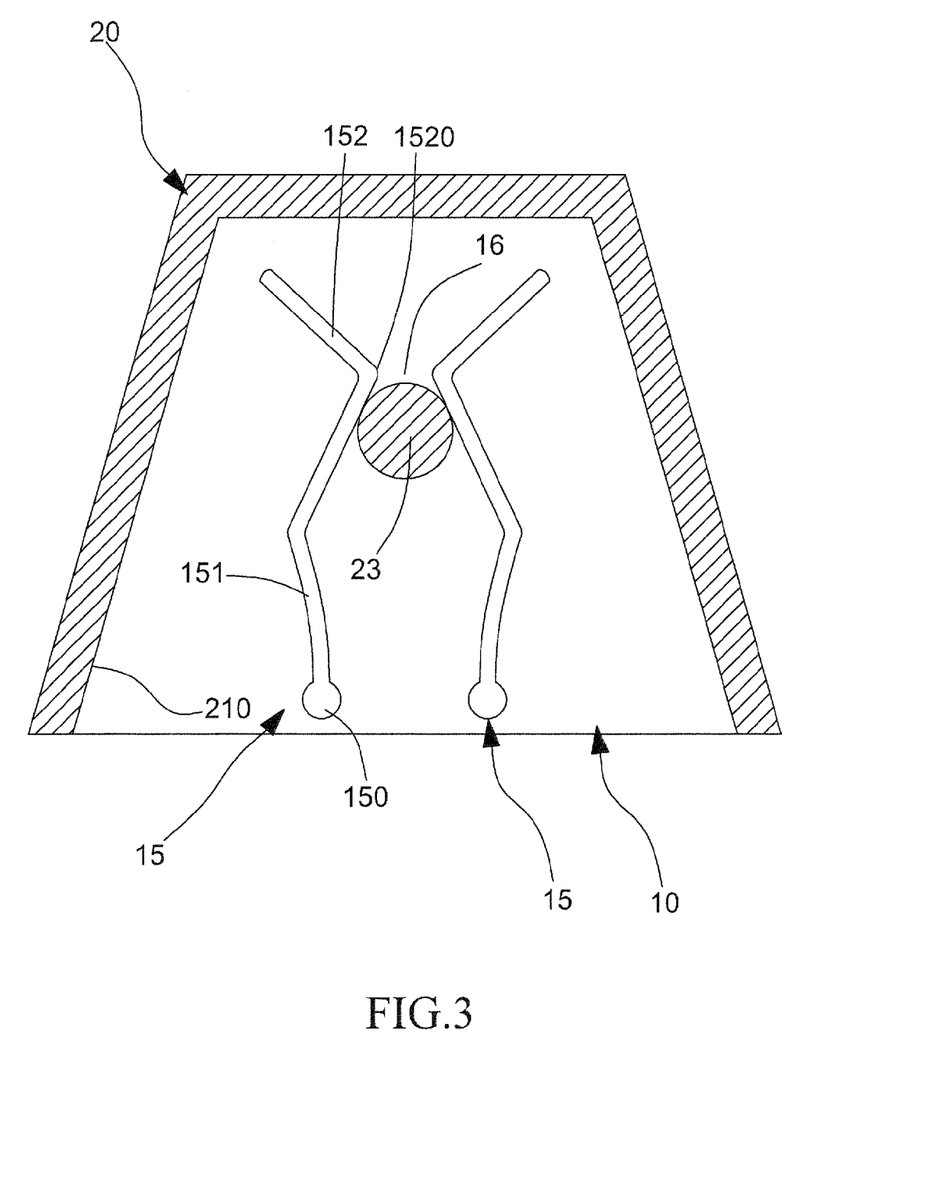
FIG. 3 is a cross-sectional view of the first embodiment of the present invention.
Figure 3A:
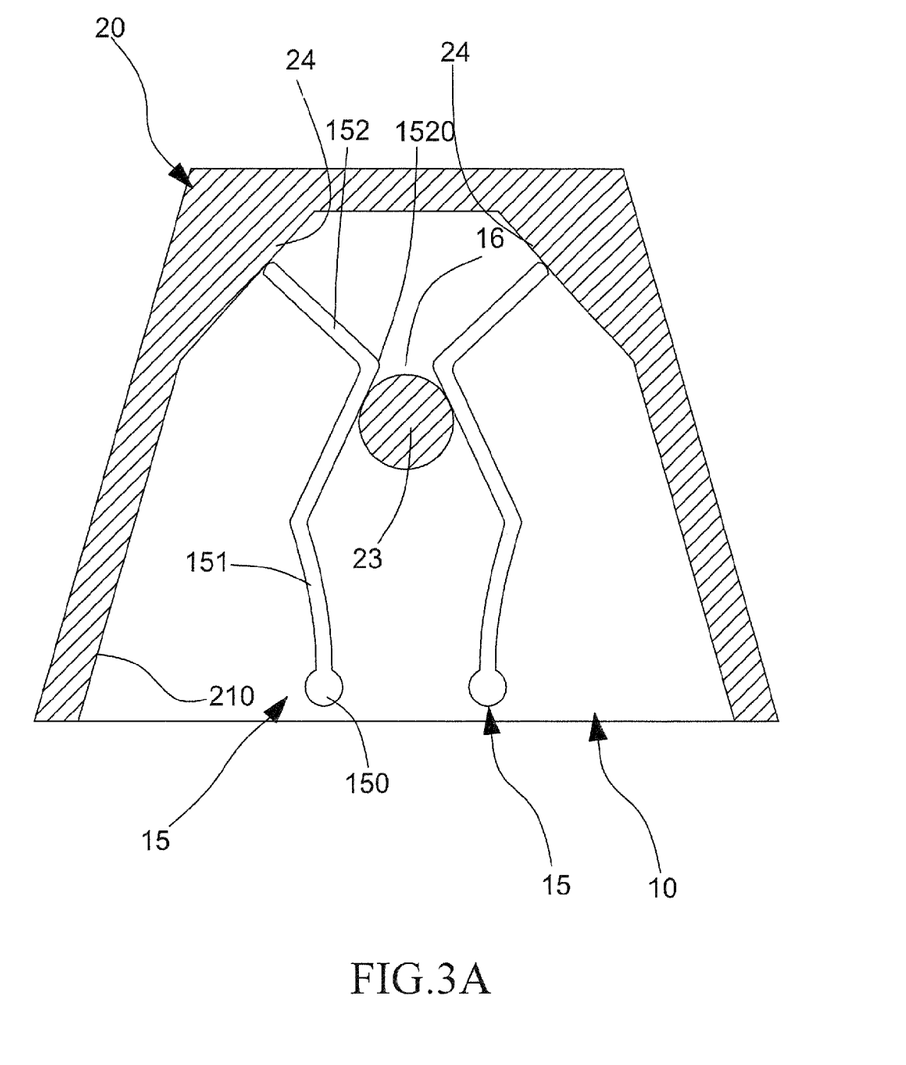
FIG. 3A is cross-sectional view showing a modification of the first embodiment of the present invention.

Referring to FIG. 3A, in case that the resilient retention clamping strips 15 of the external crown member 20 do not comprise the spring force enhancing sections, the inside surface of the external crown member 20 may still be provided with two included support surfaces 24 to respectively support distal ends of the resilient retention clamping strips 15.

Figure 7:
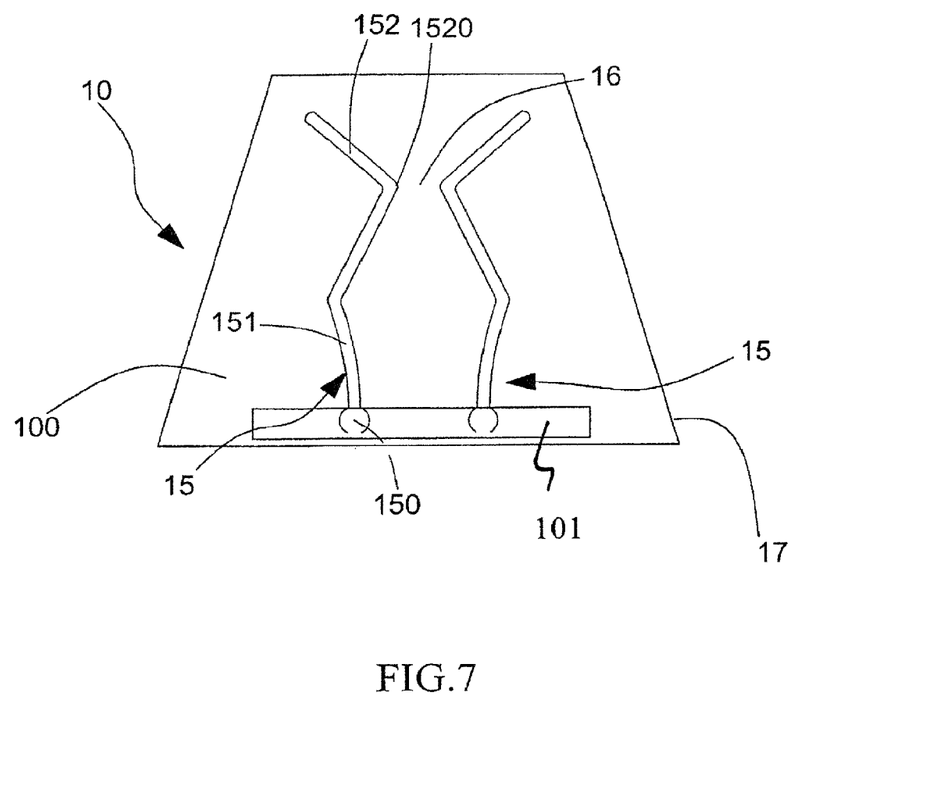
FIG. 7 is a cross-sectional view showing a third embodiment of the present invention.

Referring to FIG. 7, a detachment-prevented removable double-crown prosthetic appliance constructed in accordance with a third embodiment of the present invention comprises an internal crown member 10 to which a fixing element 101 made of metallic materials, fiber-reinforced plastics, or resins is mounted to fix the root sections 151 of the resilient retention clamping strips 15.

Further, it is noted that the present invention can be embodied by combining the second and third embodiments described above.

An example process for manufacturing a detachment-prevented removable double-crown prosthetic appliance according to the present invention will be described below:

First of all, a gingiva model is made according to the gingiva of a patient, and then the following steps are taken.

(a) Casting wax is applied to the abutment tooth of the gingiva model to make a form of an internal crown member 10 with the wax.

(b) Wax strings are attached to the outside surface 100 of the wax form of the internal crown member 10 to make a form of the resilient retention clamping strips 15.

(c) A casting process is carried out with the wax form of the internal crown member 10 to form a metal-made (such as dentistry alloys, nickel-titanium alloy, carat gold and the likes) semi-finish product of the internal crown member 10, wherein the semi-finish product of the internal crown member 10 comprises a semi-finish product of the resilient retention clamping strips 15 attached to a surface of the semi-finish product of the internal crown member 10.

(d) A dentistry ultra-thin cutting wheel or a similar tool is applied to cut from a top of the semi-finish product of each of the resilient retention clamping strips 15 to the root section 151 so as to separate the resilient retention clamping strip 15 from the outside surface 100 of the internal crown member 10 with only the root section 151 fixed to the internal crown member 10, thereby completing the formation of the resilient retention clamping strip 15.

(e) A casting wax is similarly applied to make a metallic external crown member 20 corresponding to the internal crown member 10 with a retention block 23 formed on the external crown member 20 to selectively engage the resilient retention clamping strips 15.

Besides, steps (b) to (d) can be modified by removing the wax strings for the resilient retention clamping strips so that the resilient retention clamping strips 15 are formed integrally with the internal crown member, and instead, the resilient retention clamping strip 15 are externally mounted to the internal crown member through for example welding, and under such a condition, to ensure a desired structural strength, a metal-made fixing element can be added.

With the above discussed technical solution, the present invention offers the following advantages:

(1) Since the external crown member 20 and the internal crown member 10 are coupled to each other through engagement between the resilient retention clamping strips 15 and the retention block 23, the coupling between the external crown member 20 and the internal crown member 10 is enhanced, so that the problem that the external crown member 20 is undesirably detached due to a patient chewing sticky food stuffs can be eliminated, but the user is allowed to remove the external crown member 20 from the internal crown member 10 by applying a vertical force thereto for throughout cleaning of the external crown member 20, as well as cleaning of the abutment tooth, periodontal area, and adjacent teeth. In this way, undesired detachment of the crown can be eliminated.

(2) Further, the present invention requires almost no damaging processing of adjacent natural teeth for the restoration and thus the health of the remaining natural teeth can be kept intact.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A detachment-prevented removable double-crown prosthetic appliance, comprising:
    an internal crown member, which has an outside surface to which two resilient retention clamping strips are mounted, each of the resilient retention clamping strips comprising a root section that is fixed to the outside surface of the internal crown member and a spring section extending from the root section, the spring sections of the resilient retention clamping strips being spaced by a gap that has a reduced neck portion forming a pass; and
    an external crown member, which is removably mounted to the internal crown member and has a lower inner portion forming a fitting chamber for removably fitting over the internal crown member, the fitting chamber having an inside surface that forms a retention block that is engageable with the resilient retention clamping strips by moving through the pass so as to force the spring sections of the resilient retention clamping strips to expand and deform outward, the spring sections allowing to return after the retention block moves through the pass to shrink back to clamp and thus retain the retention block, whereby the external crown member is securely coupled to the internal crown member in such a way that the external crown member is not allowed to undesirably detach;
    wherein each of the resilient retention clamping strips comprises a spring force enhancing section extending from the root section and located outside the spring section, the inside surface of the external crown member forming two inward projecting inclined support surfaces, which are respectively engageable with the two spring force enhancing sections of the resilient retention clamping strips for providing additional spring forces.

2. The detachment-prevented removable double-crown prosthetic appliance prosthetic appliance according to claim 1, wherein each of the spring sections is of an L-shape having a bend, the bends of the two spring sections opposing each other to define the pass.

3. The detachment-prevented removable double-crown prosthetic appliance according to claim 2, wherein the resilient retention clamping strips are made of a metallic material.

4. The detachment-prevented removable double-crown prosthetic appliance according to claim 3, wherein the resilient retention clamping strips are made of a metallic material that is selected from a group consisting of carat gold, dentistry alloys, stainless steels, nickel-titanium alloys and a combination thereof.

5. The detachment-prevented removable double-crown prosthetic appliance according to claim 1, wherein the external crown member and the internal crown member are made of metallic materials.

6. The detachment-prevented removable double-crown prosthetic appliance according to claim 4, wherein the external crown member and the internal crown member are made of metallic materials.

7. The detachment-prevented removable double-crown prosthetic appliance according to claim 1, wherein the root section of each of the resilient retention clamping strips has a fixed end, which is integrally formed with the outside surface of the internal crown member.

8. The detachment-prevented removable double-crown prosthetic appliance according to claim 4, wherein the root section of each of the resilient retention clamping strips has a fixed end, which is integrally formed with the outside surface of the internal crown member.

9. The detachment-prevented removable double-crown prosthetic appliance according to claim 1, wherein the root section of each of the resilient retention clamping strips has a fixed end, which is mounted to the outside surface of the internal crown member through welding, pressing, or bonding.

10. The detachment-prevented removable double-crown prosthetic appliance according to claim 4, wherein the root section of each of the resilient retention clamping strips has a fixed end, which is mounted to the outside surface of the internal crown member through welding, pressing, or bonding.

11. The detachment-prevented removable double-crown prosthetic appliance according to claim 1, wherein the internal crown member comprises a fixing element that fixes the root sections of the resilient retention clamping strips in position.

12. The detachment-prevented removable double-crown prosthetic appliance according to claim 4, wherein the internal crown member comprises a fixing element that fixes the root sections of the resilient retention clamping strips in position.

13. The detachment-prevented removable double-crown prosthetic appliance according to claim 11, wherein the fixing element is made of metallic materials, fiber-reinforced plastics, or resins.

14. The detachment-prevented removable double-crown prosthetic appliance according to claim 12, wherein the fixing element is made of metallic materials, fiber-reinforced plastics, or resins.

* * * * *